United States Patent
Burchert et al.

(10) Patent No.: US 9,804,143 B2
(45) Date of Patent: Oct. 31, 2017

(54) YARN MONITORING METHOD

(71) Applicant: Maschinenfabrik Rieter AG, Winterthur (CH)

(72) Inventors: Mathias Burchert, Ostfildern (DE); Volker Jehle, Öhningen (DE)

(73) Assignee: Maschinenfabrik Rieter AG, Winterthur (CH)

( * ) Notice: Subject to any disclaimer, the term of this patent is extended or adjusted under 35 U.S.C. 154(b) by 518 days.

(21) Appl. No.: 14/388,020

(22) PCT Filed: Mar. 15, 2013

(86) PCT No.: PCT/EP2013/055334
§ 371 (c)(1),
(2) Date: Sep. 25, 2014

(87) PCT Pub. No.: WO2013/143873
PCT Pub. Date: Oct. 3, 2013

(65) Prior Publication Data
US 2015/0033843 A1 Feb. 5, 2015

(30) Foreign Application Priority Data
Mar. 26, 2012 (DE) .................. 10 2012 102 576

(51) Int. Cl.
*G01N 33/36* (2006.01)
*B65H 63/06* (2006.01)

(52) U.S. Cl.
CPC .......... *G01N 33/365* (2013.01); *B65H 63/06* (2013.01); *B65H 2701/31* (2013.01)

(58) Field of Classification Search
CPC .................. G01N 33/365; B65H 63/06
See application file for complete search history.

(56) References Cited

U.S. PATENT DOCUMENTS

| | | | | |
|---|---|---|---|---|
| 4,513,921 A * | 4/1985 | Imoda | ............... | B65H 69/00 242/475.1 |
| 4,804,151 A * | 2/1989 | Kathke | ............... | B65H 54/22 242/475.4 |
| 4,984,749 A | 1/1991 | Matsui et al. | | |
| 5,022,596 A * | 6/1991 | Wey | ............... | B65H 63/00 242/474 |
| 5,592,849 A * | 1/1997 | Nakade | ............... | B65H 63/06 57/265 |
| 5,834,639 A * | 11/1998 | Meier | ............... | G01N 33/365 73/159 |
| 5,915,279 A * | 6/1999 | Cantrall | ............... | G01B 11/105 250/559.11 |
| 6,025,727 A * | 2/2000 | Inkpen | ............... | G01N 33/365 324/663 |
| 6,110,403 A * | 8/2000 | Binner | ............... | B65H 63/00 264/103 |
| 6,244,030 B1 * | 6/2001 | Arb | ............... | B65H 63/065 57/264 |
| 6,270,033 B1 | 8/2001 | Haasen et al. | | |
| 6,374,152 B1 | 4/2002 | Wepfer et al. | | |
| 6,380,548 B1 | 4/2002 | Henze et al. | | |
| 7,424,800 B2 | 9/2008 | Biermann et al. | | |
| 2002/0074445 A1 * | 6/2002 | Oehrl | ............... | B65H 63/036 242/475.4 |
| 2002/0161470 A1 * | 10/2002 | Kusuzono | ............... | B65H 49/12 700/142 |
| 2007/0022728 A1 * | 2/2007 | Biermann | ............... | B65H 63/065 57/265 |
| 2008/0197522 A1 * | 8/2008 | Schemken | ............... | D01D 11/00 264/40.3 |
| 2010/0157301 A1 * | 6/2010 | Miyahara | ............... | B65H 63/0324 356/431 |

FOREIGN PATENT DOCUMENTS

| | | |
|---|---|---|
| CN | 1530631 | 9/2004 |
| DE | 101 41 963 A1 | 3/2003 |
| DE | 10 2005 017 606 A1 | 10/2006 |
| DE | 10 2008 017 258 A1 | 10/2009 |
| DE | 10 2008 037 758 A1 | 2/2010 |
| EP | 1 712 507 A1 | 10/2006 |
| WO | WO 99/36746 | 7/1999 |
| WO | WO 2011/038524 A1 | 4/2011 |
| WO | WO 2012/079181 A1 | 6/2012 |

OTHER PUBLICATIONS

German Patent Office Search Report, Dec. 3, 2012.
PCT Search Report, Jun. 3, 2013.
PCT International Preliminary Report on Patentability, Mar. 15, 2013.
Office Action from Chinese Patent Office, Dec. 16, 2015.

* cited by examiner

*Primary Examiner* — Shaun R Hurley
(74) *Attorney, Agent, or Firm* — Dority & Manning, P.A.

(57) ABSTRACT

The invention relates to a method for monitoring the quality of a yarn on a textile machine, wherein the yarn passes a monitoring unit of the textile machine, with the aid of which at least one measured variable (M) which is dependent on a physical parameter of the yarn is determined, and wherein the measured variable (M), or a variable derived therefrom, is evaluated with respect to the position thereof with regard to at least one reference value (R). According to the invention, it is proposed that the selection of the reference value(s) (R) takes place taking into account one or more characteristic variables of the yarn, said characteristic variables being yarn-specific and defined prior to evaluating the measured variable (M). Furthermore, a textile machine is proposed which comprises at least one monitoring unit for monitoring at least one physical parameter of the yarn, and at least one controller which is operatively connected to the monitoring unit. The textile machine is characterized in that the controller is configured to monitor the yarn quality according to one or more of the preceeding claims.

13 Claims, 3 Drawing Sheets

US 9,804,143 B2

YARN MONITORING METHOD

FIELD OF THE INVENTION

This invention refers to a method for monitoring the quality of a yarn on a textile machine, wherein the yarn passes through a monitoring unit of the textile machine with whose assistance at least one measured variable that depends on a physical parameter of the yarn is determined and wherein the measured variable or a variable derived from it is evaluated with regard to its position with at least one reference value. Apart from that, a textile machine is proposed that includes at least one monitoring unit for monitoring at least one physical parameter of the yarn and at least one control that is operationally connected to the monitoring unit.

BACKGROUND

In the state of the art, it is customary to monitor yarn quality either right after manufacturing (for example, after the spinning position of a rotor spinning machine) or during a handling step following production (for example, during rewinding from one yarn spool to another). As a rule, physical parameters or measured values dependent on them are monitored in this step. It is known, for example, that yarn thickness or hairiness can be analyzed by evaluating the shadow cast by the yarn on a control surface and using this to draw conclusions about yarn quality.

So reliable statements about yarn quality can be made from the measured values determined, however, a reference value used for comparing the measured values determined is always needed. If the measured values deviate from the reference value within predefined limits, then it is assumed that yarn quality conforms to specifications. Generic yarn monitoring is shown in DE 10 2005 017 606 A1, for example.

The reference value is finally determined at the start of a production process by monitoring the measured variable to be monitored over a certain time period and converting it to a reference value.

However, the disadvantage of the state of the art is that the initial determination of the reference value is time-dependent and contains errors. In particular, the quality of the entire yarn batch deviates from the target when the initial determination of the reference value is performed erroneously for any reason.

SUMMARY OF THE INVENTION

A task of this invention is therefore to suggest a method for monitoring yarn quality on a textile machine that does not have the disadvantages mentioned above. Furthermore, a textile machine that makes this corresponding quality monitoring possible should be proposed. Additional objects and advantages of the invention will be set forth in part in the following description, or may be obvious from the description, or may be learned through practice of the invention.

The task is solved by a method and a textile machine having the characteristics described herein.

The method for monitoring yarn quality according to the invention is thus characterized in that the selection of the reference value(s) takes place considering one or several yarn-specific characteristic variables of the yarn defined before the evaluation takes place.

Thus, the reference value(s) is/are not constantly recalculated at the start of yarn manufacturing or another handling but is/are preferably made available to the textile machine already before actual quality monitoring starts.

The appropriate reference value is selected here based on the characteristic variable(s) mentioned above. Whereas the characteristic variables (explained in more detail below) can reflect the (for example, physical) properties of the yarn (e.g. its hairiness) to be manufactured, it is possible to use a yarn-specific code as characteristic variable, for example. If, for example, cotton yarn having yarn count X, twist Y and hairiness Z should be manufactured, then the operator (or control) of the textile machine knows that he (or it) must select the associated reference value 123 and make it available to the textile machine. Thus, before yarn production starts, the corresponding reference value 123 is read in or loaded in the monitoring system. During the course of production, the monitored measured value (which reflects yarn thickness, for example) is compared with the above-mentioned reference value. In the final analysis, yarn with reproducible properties can be manufactured again and again after a batch change too because the same reference value is always available or selected for a certain yarn (which can be defined by one or more characteristic variables).

The reference value is selected either through the yarn-specific code number mentioned above but it is also conceivable to consider several characteristic variables such as yarn count, hairiness or the fiber material to be spun when the reference value is selected.

Finally, the reference values can be either read in a central control unit of the textile machine, which finally receives the individual measured variables from the individual units (e.g. spinning or spool positions) and compares each one with the reference value. However, it is also conceivable for the reference values to be transmitted to the individual monitoring units of the respective units so the reference value-measured variable comparison can take place directly in the respective unit. If excessive deviations from the measured variable are detected by the reference value(s) (that create the corresponding limits), then an alarm is heard and/or optical indicator seen or there is an intervention in the control of the corresponding unit in order to regulate the monitored measured variable or the yarn's physical parameters that influence the measured variable to fall back to an admissible range.

Here, it is especially advantageous if the corresponding reference values are deposited in a database and read out if needed (i.e. preferably before quality monitoring starts) for transmission to the control unit of the textile machine (naturally, the database can also be part of the control so that the corresponding transmission would become superfluous). The reference values for this are preferably coupled with one or several of the above-mentioned characteristic variables to allow or facilitate the selection of the appropriate reference value(s) based on the characteristic variable.

It is particularly advantageous to consider yarn thickness as a physical parameter, in which case the determination of the measured variable dependent on it is done preferably with the help of an optical system that evaluates, for example, the shadow cast by the yarn when lit to find out its geometry. For this, a line camera that evaluates the pixels of one pixel row (or several lying beside one another) can be used, for example, to know whether a shadow has been recognized or not. The evaluation finally delivers the thickness of the yarn running through—needless to say, it is assumed that the camera is placed so that the pixel rows do not run parallel to the yarn's longitudinal axis). Therefore, the yarn passes through a light source that generates visible or invisible light so a shadow is generated on the corresponding control surface. The shadow or its spatial extension in one or several defined directions is recorded with the help of a camera or another system and converted to yarn's width, which, in the final analysis represents the above-mentioned physical parameter, while the measured variable can be, for example, the current intensity of a measured current generated by the camera depending on the above-mentioned geometry of the shadow. It is also conceivable for the measured variable to represent the number of pixels that detect a shadow.

It is additionally advantageous if yarn hairiness, yarn material, yarn uniformity, yarn quality, yarn stiffness, the extent of the yarn's twist and/or yarn tension are considered when the reference value is selected. In principle, all characteristic variables that allow a yarn to be identified are conceivable so that, for a certain yarn being produced by the machine or that should be handled in another way, one or several associated reference values can be selected from the database.

It is also advantageous if an individual value is selected as a reference value, in which case the reference value serves as target value of the measured variable and the magnitude of the measured variable or a magnitude derived from it is evaluated with respect to its absolute deviation from the reference value. In this way, it is possible to add up the positive and negative deviations over time, for example. An alarm or adjustment of selected parameters of the textile machine's monitored unit (e.g. the rotor's rpm on a spinning position of a rotor spinning machine) finally takes place when the value added up over a certain time period lies above or below the corresponding limits.

It can also be advantageous if the reference value is an individual value and the measured variable or a variable derived from it is evaluated to find out whether its magnitude lies between a minimum value lying below the reference value and a maximum value lying above the reference value. As long as the measured variable (or its magnitude) lies between the minimum and maximum value, the associated control will assume that yarn quality complies with specifications. If one of the values is exceeded, it is a sign that there are material or production faults. As a result of that, manual or also automatic interventions in the control for the purpose of adjusting individual operational parameters of the textile machine can take place. The emission of the corresponding alarm is also conceivable to make an operator aware of the deviations.

It is especially advantageous if a first reference value defines an admissible minimum value and a second reference value an admissible maximum value and that verification as part of quality monitoring takes place to see whether the magnitude of the measured variable or a magnitude derived from it lies between the minimum and maximum value. In this case, the setting of the reference values is limited to selecting two limits between which the measured variable should lie. If, for example, it is known that a certain yarn (defined by the characteristic variables of material, strength, extensibility, etc.) should have a yarn thickness within the range of A and B, then the magnitudes of A and B are stored in the database as reference values for a yarn with these characteristic variables. If this yarn should now be produced, then the above-mentioned reference values are read out from the database and forwarded to the corresponding control or individual monitoring units of the textile machine.

It is also advantageous if the measured variable is continuously determined and evaluated. Here, "continuously" is understood to be either a monitoring that actually records measured values all the time to obtain a real time value of the measured variable uninterruptedly but, alternately, it is also conceivable for the determination or evaluation to take place in predefined time intervals and thus to be continuous as well. It is furthermore possible to statistically evaluate several individual measured values of the measured variable so that each minute, a mean value is obtained from the measured values recorded in the preceding minute, for example, and the mean value is compared with the reference value(s).

It is furthermore advantageous if the measured variable is determined in the form of absolute values because, as a result of this, dependencies caused by errors can be excluded from other magnitudes. Thus, the measured values between individual yarn batches can be easily compared and, in particular, it is ensured that the measured variable of yarn XY is still nonetheless significant and can be compared with the associated reference value stored in the database if days or weeks have elapsed between the production of two XY batches and during this time the textile machine produced or otherwise handled yarn AB, which has other properties.

It is likewise advantageous to determine the reference values, wherein the previously defined characteristic variable(s) of a reference yarn and the measured variable of the reference yarn dependent on the above-mentioned physical parameter of the yarn is/are determined as part of the reference measurements, in which case one or several reference values are determined based on the measured variable or a magnitude derived from it, and whereby the characteristic variable(s) and the reference value(s) are stored in the database correlated with one another. In other words, the data of the database are generated because the measured variable is determined during the production of a yarn that is being included in the database before or after its production. Likewise, the necessary characteristic variable(s) are determined by means of their or the reference value(s) finally selected from the database before a subsequent production process of a yarn that is as similar as possible to the reference yarn. Finally, in the database, the reference values are associated with the yarn's relevant characteristic variable(s) so that at a later, arbitrary point in time, the database can provide the reference value(s) after the characteristic variable(s) is/are entered.

It is particularly advantageous if the yarn's quality is verified periodically and preferably when a maximum value of the reference value is exceeded or a minimum value of the reference value is not reached and the reference value(s) are reset or maintained constant depending on the quality test result. In other words, the reference values stored in the database do not have to be maintained constant forever. It is, for example, conceivable to store a reference value A or the minimum and maximum values B and C for a yarn with the characteristic variables X, Y and Z. If now the monitored measured variable does not reach the minimum value B, then this initially signals the control and/or operator that yarn quality does not meet specifications. If, however, a corresponding yarn inspection (of the textile machine or in a separate testing location) carried out manually or with the help of the respective devices determines that yarn quality nonetheless complies with the specifications set for yarn having the characteristic variables X, Y and Z, then the reference value A or the minimum and maximum values B and C can be adjusted in the database. This occurs, for example, when the values mentioned above are displaced in such a way that the magnitude of the measured variable (pertaining to the original values lying outside the admissible range) once again lies between the values of B and C. The database can therefore be adjusted continuously so that a reference value set one time does not have to mean that subsequent adjustments are impossible (for example, the difference between minimum and maximum value can be also reduced or enlarged, if necessary, if the yarn's purchaser changes his quality requirements made to the yarn).

It is especially advantageous if the reference value(s) correlated with the characteristic variable(s) of the yarn are taken from the database before the yarn's monitoring and used for quality monitoring. Thus, the reading out always takes place preferably when either the yarn to be produced or handled by the textile machine should be changed. However, if the textile machine stops for a longer period, then it is not necessary to read out the reference value(s) again if the same yarn should be produced or otherwise handled (e.g. rewound) and the measured variable is determined as absolute value.

It is especially advantageous if the database is stored in a control unit of the textile machine or in a monitoring unit. Needless to say, it is also possible to place the database away from the textile machine and to transfer the data manually or by means of the corresponding network connections to the textile machine when the yarn to be produced or otherwise handled is changed. In this case, the database would serve multiple textile machines that could be set up in different production facilities.

Finally, the textile machine according to the invention is characterized by the fact that it has a control designed to monitor yarn quality according to the preceding description. With regard to the possible variants and advantages, we refer to the description provided above and below. In particular, this applies to the current structural characteristics of the textile machine (such as, for example, the already described optical system for measuring the geometry of the yarn to be monitored that casts a shadow when lit by a light source). Generally, the textile machine can be a one for producing yarn (e.g. a rotor, air or also ring spinning machine). Likewise, the textile machine can serve for processing already produced yarn further or handle it in some other way. For example, the textile machine can be designed as spooling machine with whose help yarn can be rewound from one spool to another. Moreover, it should be pointed out here that the textile machine can have one or also many monitoring units to monitor only one or many yarns passing through or leaving the respective production or handling units of the textile machine.

BRIEF DESCRIPTION OF THE DRAWINGS

Additional advantages of the invention are described in the following embodiments which show.

DETAILED DESCRIPTION

Figure 1:
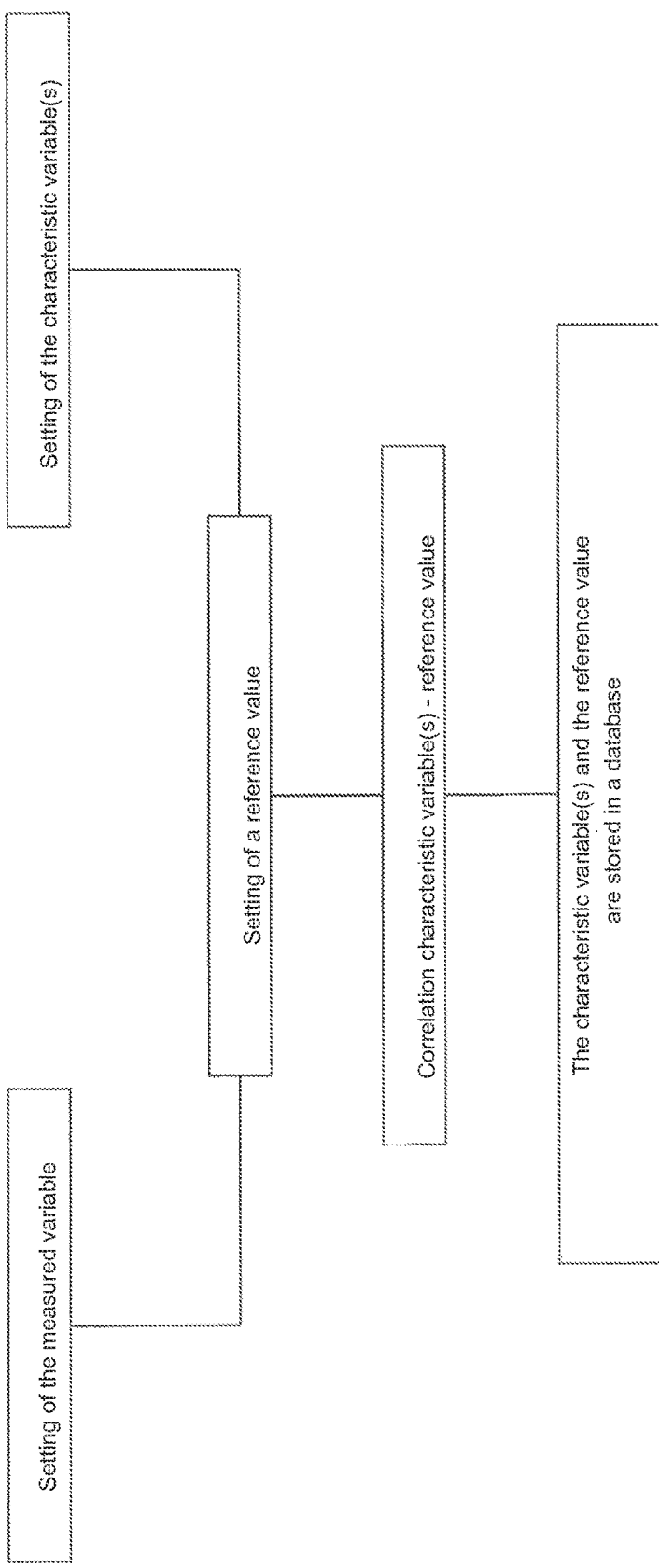
FIG. 1 a method for generating a reference value.

Reference will now be made to embodiments of the invention, one or more examples of which are shown in the drawings. Each embodiment is provided by way of explanation of the invention, and not as a limitation of the invention. For example features illustrated or described as part of one embodiment can be combined with another embodiment to yield still another embodiment. It is intended that the present invention include these and other modifications and variations to the embodiments described herein.

FIG. 1 depicts schematically a possible process for establishing and storing a necessary reference value in a database for executing the method according to the invention.

First of all, a measured variable is defined that in the subsequent monitoring of yarn quality on a textile machine is recorded so it can serve as basis for quality assessment. For example, a power signal generated by a camera can be a measured variable, in which case the camera, in turn, can be designed to detect the geometry—especially the width—of the shadow, cast by the yarn when lit. Here, the magnitude of the measured variable therefore depends on the yarn's width (=spatial extension perpendicular to the yarn's longitudinal axis), i.e. the width of the yarn is monitored.

After setting the measured variable, a reference value for the measured variable is defined. The reference value represents the value that the measured variable should take when yarn quality is perfect. Needless to say, additional or alternative reference values in form of admissible minimum and maximum values can also be defined, between which the measured variable should lie if yarn quality is perfect.

So the reference values can always be retrieved from a database containing the reference values when a certain yarn should be manufactured or otherwise handled by the textile machine, the reference value(s) is/are not only stored as value(s) in the database. Rather, the linking with one or several yarn-specific characteristic variables with whose help the corresponding reference values can always be allocated to one yarn in particular takes place. Codes (e.g. alphanumeric ones) or other yarn-specific characteristic variables as well, such as yarn material, yarn twist, yarn weight related to the length, yarn hairiness, etc. can be used. Crucial is merely that once the reference values are set, they can still be assigned unmistakably to a certain yarn later.

In other words, the solution according to the invention allows a certain yarn (e.g. cotton yarn with hairiness A, strength B and yarn count C) to be monitored always equally. Thus, whenever such a yarn should be monitored, the associated reference value is forwarded to the control of the textile machine or to its corresponding yarn monitoring units, so that the point of reference of the monitoring is always the same. If, additionally, the characteristic variable is measured by detecting absolute values, then the monitoring unit does not have to be recalibrated before each change of the yarn, as is customary in state of the art. Rather, yarn quality can be reliably monitored—especially in a reproducible way—always from the start.

Figure 2:
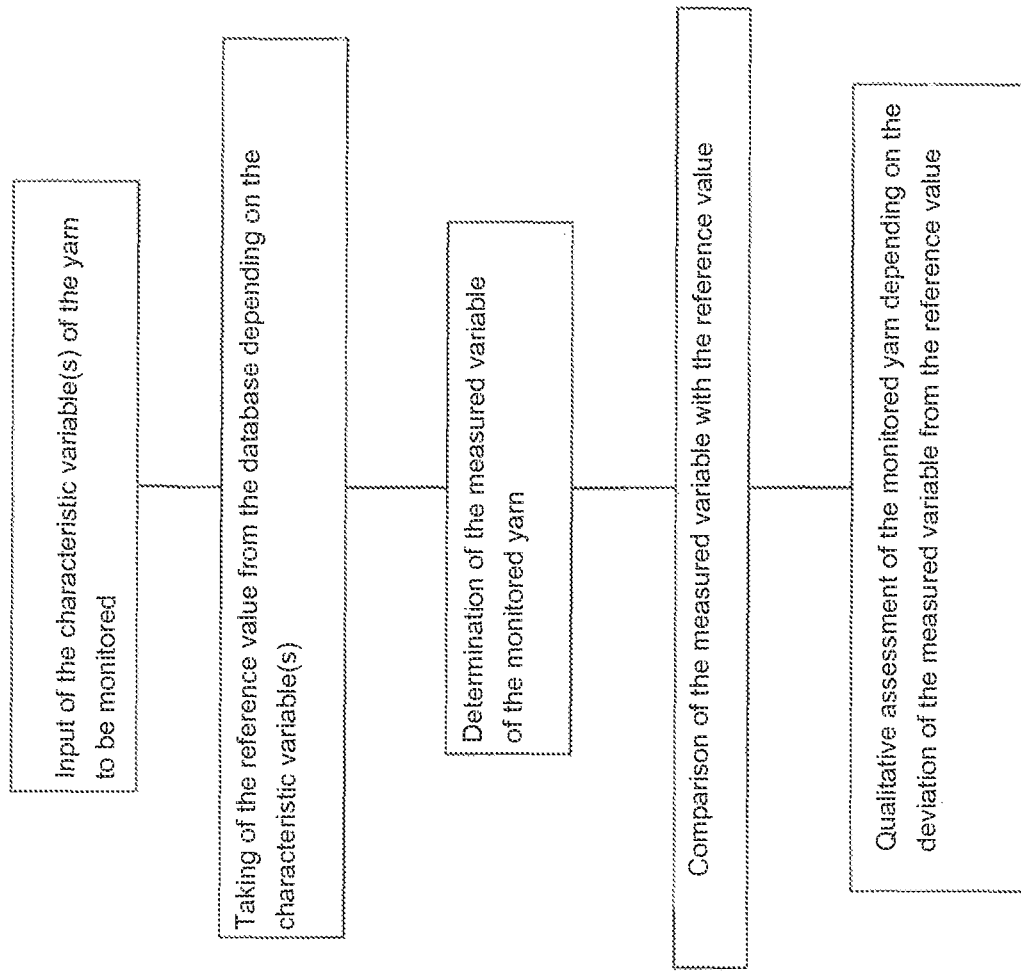
FIG. 2 a method for selecting a reference value from a database.

FIG. 2 shows a possible approach taken for selecting the correct reference value or corresponding minimum or maximum values.

First, the characteristic variable(s) of the yarn to be monitored must be entered in the database, which, in the final analysis, provides the desired values linked to the characteristic variable(s). The reference value(s) is/are finally transferred to the control of the textile machine or its corresponding monitoring units and serve as basis for subsequent quality monitoring.

As part of monitoring, the yarn's measured variable is finally determined by preferably measuring continuously a measured value that represents the measured variable and comparing it with the reference value. A measured variable that lies within predefined limits (admissible minimum value, admissible maximum value) indicates acceptable yarn quality. If the measured variable exceeds or does not reach the admissible values mentioned above, yarn quality no longer complies with specifications. In this case, either an alarm is emitted or—if the yarn is being monitored immediately after production—an intervention in the control of the respective production unit takes place. In the end, the goal can be to regulate the production parameters in such a way that the measured variable always lies within the above-mentioned limits.

Figure 3:
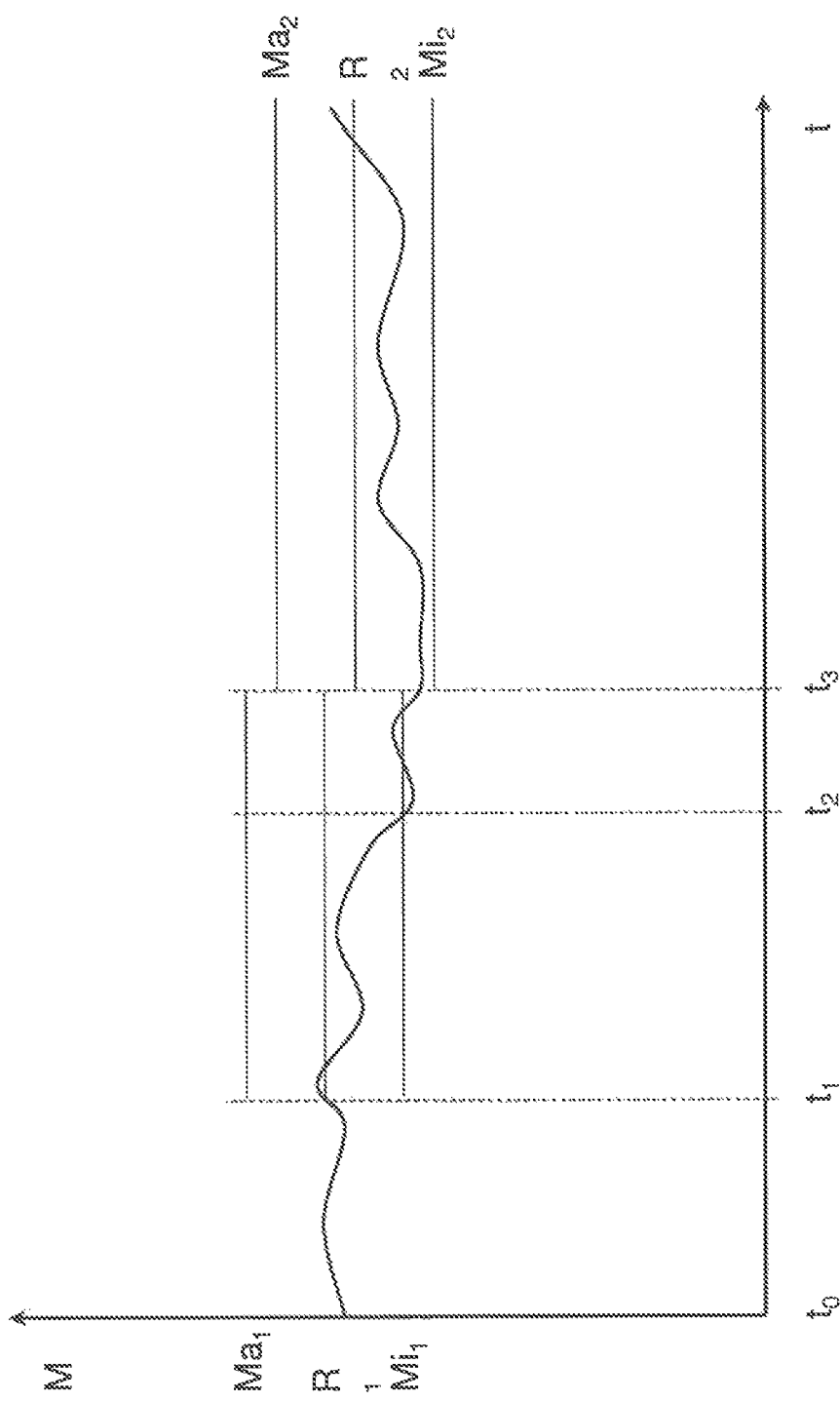
FIG. 3 a possible chronological sequence of a measured variable.

FIG. 3 finally shows a possibility to determine or adjust the reference value. Here, M (y axis) stands for the measured variable and t (x axis) for time.

If there is still no reference value R for a certain yarn, then the type of measured variable M (e.g. the signal of a line scan camera that monitors yarn width) to be monitored later is established. Afterwards, the recording of the measured variable M is started while the corresponding yarn passes through the monitoring unit ($t_0$: start of recording measured variable M). If yarn quality complies with specifications, the currently available magnitude of the measured variable M (or a value derived from it) in the point in time $t_1$ is defined as reference value $R_1$ and stored in the database, linking it with one or several typical characteristic variables of the yarn (hairiness, yarn count, yarn code and/or other variables that characterize a certain yarn). If a yarn with similar properties should later be monitored once again at a later point in time, then a reference value $R_1$ is available that can be always be retrieved from the database.

If subsequent yarn monitoring (in FIG. 3 it is exemplarily the point in time $t_2$) determines that the measured variable M does not reach an admissible minimum value $Mi_1$ (alternatively: exceeds an admissible maximum value $Ma_1$), then it could be possible for the textile machine operator to check yarn quality. If the checking determines that quality still complies with specifications, then the reference value R can be corrected from the value $R_1$ to the value $R_2$. The corrected value is finally stored in the database (or the old values are overwritten by the corrected ones) together with a correspondingly corrected minimum value $Mi_2$ and a correspondingly corrected maximum value $Ma_2$.

Afterwards, the new reference value $R_2$ or the two reference values $Ma_2$ and $Mi_2$ finally serve as new reference variables that can be used for monitoring yarn quality.

This invention is not limited to the embodiment shown and described. Variations within the framework of the patent claims are just as possible as a combination of the characteristics, even if they are shown and described in different embodiments.

The invention claimed is:

1. A method for monitoring quality of a yarn in a textile machine, comprising:
passing the yarn through a monitoring unit of the textile machine and determining a measured variable that depends on one or more continuous physical characteristics of the yarn;
evaluating the measured variable (which encompasses a variable derived from the measured variable) with regards to a reference value;
before evaluating the measured variable, selecting the reference value based on one or more yarn-specific physical characteristic variables of the yarn; and
wherein continuous yarn thickness is the yarn-specific physical characteristic variable of the yarn and the reference value is selected based on any one or combination of the following yarn characteristic variables: yarn hairiness, yarn material, yarn uniformity, yarn fineness, yarn stiffness, extent of yarn twist, or yarn tension.

2. The method as in claim 1, wherein the reference value is selected from a database that includes multiple reference values based on the yarn-specific physical characteristic variables of the yarn.

3. The method as in claim 1, wherein the measured variable varies as yarn thickness changes and is determined by an optical system that evaluates geometry of the yarn by a shadow the yarn casts.

4. The method as in claim 1, wherein the reference value is an individual value that serves as a target value of the measured variable, and the measured variable is evaluated based on deviation from the measured variable form the reference value.

5. The method as in claim 4, wherein the measured variable is evaluated based on whether it lies between a minimum value below the reference value and a maximum value above the reference value.

6. The method as in claim 4, wherein the reference value includes a first reference value that defines an admissible minimum value, and a second reference value that defines an admissible maximum value, wherein the measured variable is evaluated based on whether it lies between the first reference value and the second reference value.

7. The method as in claim 1, wherein the measured variable is continuously determined and evaluated.

8. The method as in claim 1, wherein the measured variable is determined as an absolute value.

9. The method as in claim 1, wherein the reference values are determined based on specific physical characteristics of a reference yarn, and the reference values and respective specific physical characteristics are correlated with each other and stored in a database.

10. The method as in claim 9, wherein the reference values are periodically checked and reset if the reference value exceeds a maximum value or falls below a minimum value.

11. The method as in claim 9, wherein before monitoring of the yarn, the references values correlated with the specific physical characteristics that determine the measured variable are downloaded from the database.

12. The method as in claim 11, wherein the database is stored in a control unit for the textile machine or in the monitoring unit.

13. A textile machine, comprising a monitoring unit for monitoring quality of a yarn produced by the textile machine in accordance with the method of claim 1.

* * * * *